(12) United States Patent
Nagae et al.

(10) Patent No.: US 10,130,324 B2
(45) Date of Patent: *Nov. 20, 2018

(54) IMAGE ANALYSIS DEVICE AND X-RAY DIAGNOSTIC APPARATUS

(71) Applicant: TOSHIBA MEDICAL SYSTEMS CORPORATION, Otawara-Shi (JP)

(72) Inventors: Ryoichi Nagae, Nasushiobara (JP); Yoshinori Shimizu, Nasushiobara (JP); Nobuo Kobayashi, Nasushiobara (JP); Keisuke Nakamura, Utsunomiya (JP); Kunio Shiraishi, Otawara (JP)

(73) Assignee: TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/795,430

(22) Filed: Oct. 27, 2017

(65) Prior Publication Data

US 2018/0055472 A1    Mar. 1, 2018

Related U.S. Application Data

(63) Continuation of application No. 14/533,622, filed on Nov. 5, 2014, now Pat. No. 9,833,211.

(30) Foreign Application Priority Data

Dec. 11, 2013   (JP) ................. 2013-255701

(51) Int. Cl.
*G06K 9/00* (2006.01)
*A61B 6/00* (2006.01)
*G06T 11/00* (2006.01)

(52) U.S. Cl.
CPC .............. *A61B 6/507* (2013.01); *A61B 6/461* (2013.01); *A61B 6/481* (2013.01); *A61B 6/486* (2013.01);
(Continued)

(58) Field of Classification Search
None
See application file for complete search history.

(56) References Cited

U.S. PATENT DOCUMENTS 6,463,167 B1   10/2002   Feldman
7,912,528 B2   3/2011   Krishnan
(Continued)

FOREIGN PATENT DOCUMENTS

DE   10 2007 024 450 A1   11/2008
DE   10 2011 006 520 A1   10/2012
(Continued)

*Primary Examiner* — Gandhi Thirugnanam
(74) *Attorney, Agent, or Firm* — Oblon, McClelland, Maier & Neustadt, L.L.P.

(57) ABSTRACT

According to one embodiment, an image analysis device includes a parameter value acquisition unit, a color allocation unit and a time phase image generation unit. The parameter value acquisition unit acquires a parameter value per pixel, on the basis of time variation of pixel values per pixel corresponding to the same region of an object in image data of a plurality of sequential DSA images. The color allocation unit generates a color map in which a (chromatic) color in accordance with the parameter value is allocated per pixel corresponding to the same region of the object. The time phase image generation unit generates color image data of time phase images respectively corresponding to a plurality of time phases, by reflecting information in accordance with pixel values of the DSA images to each pixel of the color map.

14 Claims, 12 Drawing Sheets

(52) U.S. Cl.
    CPC ............ *A61B 6/504* (2013.01); *G06T 11/001* (2013.01); *H05K 999/99* (2013.01)

(56) References Cited

U.S. PATENT DOCUMENTS

| | | | |
|---|---|---|---|
| 8,073,224 B2 | 12/2011 | Strobel et al. | |
| 9,119,550 B2 | 9/2015 | Lee | |
| 9,230,323 B2 | 1/2016 | Kobayashi | |
| 9,833,211 B2 * | 12/2017 | Nagae | A61B 6/507 |
| 9,833,212 B2 * | 12/2017 | Nagae | A61B 6/5211 |
| 2005/0053267 A1 | 3/2005 | Mostafavi | |
| 2005/0288589 A1 | 12/2005 | Houle | |
| 2008/0027319 A1 | 1/2008 | Gardner | |
| 2008/0097207 A1 | 4/2008 | Cai | |
| 2009/0110252 A1 | 4/2009 | Baumgart | |
| 2010/0259550 A1 | 10/2010 | Baumgart et al. | |
| 2010/0329523 A1 | 12/2010 | Ostermeier | |
| 2011/0142318 A1 | 6/2011 | Chen | |
| 2012/0114217 A1 | 5/2012 | Mistretta | |
| 2013/0077839 A1 | 3/2013 | Horz et al. | |
| 2013/0343625 A1 * | 12/2013 | Samsonov | G06T 11/005 382/131 |
| 2013/0345559 A1 | 12/2013 | Haemmerich et al. | |
| 2015/0071520 A1 | 3/2015 | Takemoto | |
| 2015/0150526 A1 * | 6/2015 | Ohishi | A61B 6/463 378/62 |
| 2015/0161800 A1 * | 6/2015 | Nagae | A61B 6/504 378/62 |
| 2015/0201897 A1 | 7/2015 | Kyriakou | |
| 2015/0332455 A1 | 11/2015 | Kobayashi | |
| 2016/0015348 A1 | 1/2016 | Ohishi | |
| 2016/0022236 A1 * | 1/2016 | Ohishi | A61B 6/481 600/431 |
| 2016/0078621 A1 | 3/2016 | Nagae | |
| 2016/0089097 A1 | 3/2016 | Ohishi | |
| 2016/0143605 A1 * | 5/2016 | Nagae | A61B 6/5211 378/62 |

FOREIGN PATENT DOCUMENTS

| | | |
|---|---|---|
| JP | 2006-87631 | 4/2006 |
| WO | WO 2006/051831 A1 | 5/2006 |
| WO | WO 2007/052634 A1 | 5/2007 |
| WO | WO 2013/183775 A1 | 12/2013 |

\* cited by examiner

IMAGE ANALYSIS DEVICE AND X-RAY DIAGNOSTIC APPARATUS

CROSS-REFERENCE TO RELATED APPLICATION

This application is a continuation of U.S. application Ser. No. 14/533,622, filed Nov. 5, 2014, which is based upon and claims the benefit of priority from Japanese Patent Application No. 2013-255701, filed on Dec. 11, 2013;

The entire contents of which are incorporated herein by reference.

BACKGROUND OF THE INVENTION

1. Field of the Invention

Embodiments described herein relate generally to an image analysis device and X-ray diagnostic apparatus.

2. Description of the Related Art

As endovascular therapy, a vasodilation operation in which blood vessels are dilated from inside by using a catheter or the like and a vascular embolus operation which aims to necrotize a tumor by embolizing the blood vessels providing nutrition to the tumor are known. In order to confirm the effect of such vascular therapy, DSA (Digital Subtraction Angiography) images are used (for example, see Japanese Patent Application Laid-open (KOKAI) Publication No. 2006-87631).

The DSA images are obtained by, for example, sequentially imaging the same region of a patient before and after administration of a contrast agent with the use of an X-ray diagnostic apparatus. More specifically, a plurality of subtraction images obtained by subtracting a mask image before administration of the contrast agent from the image of each time phase after administration of the contrast agent so as to respectively correspond to the time phases are defined as the DSA images.

In conventional technology, the sequential DSA images are generated before and after an operation respectively, and a reader confirms the effect of the operation by visually comparing these DSA images. The confirmation of the effect of the operation means judgment (identification) of a bloodstream improving region in the case of the vasodilation operation and means judgment of a bloodstream occluded region in the case of the vascular embolus operation, for example.

If comparison between moving image display of the DSA images before the operation and moving image display of the DSA images after the operation does not clearly indicate degree of bloodstream improvement or a position of a bloodstream occluded region, a reader selects an arbitrary one image out of the DSA images before the operation, selects an arbitrary one image out of the DSA images after the operation, and then compares these selected two images as still pictures. It is not necessarily easy to identify a slight difference in bloodstream between before and after the operation by visually comparing the DSA images before and after the operation.

Therefore, a novel technology to enable visual confirmation of a region with changed bloodstream amount based on DSA images before an operation or based on DSA images after start of an operation more easily than conventional technology has been desired.

For example, a novel technology to enable visual confirmation of the region with changed bloodstream amount after an operation such as a bloodstream improving region after the vasodilation operation and a bloodstream occluded region after the vascular embolus operation, on the basis of the DSA images before and after an operation, more easily than conventional technology has been desired.

DETAILED DESCRIPTION

Hereinafter, examples of aspects which embodiments of the present invention can take will be explained per aspect.

(1) According to one embodiment, an image analysis device includes a DSA image acquisition unit, a parameter value acquisition unit, a color allocation unit and a time phase image generation unit.

The DSA image acquisition unit acquires a plurality of sequential (time-series) DSA images of the same object.

The parameter value acquisition unit acquires a parameter value per pixel, on the basis of time variation of pixel values per pixel corresponding to the same region of the object in the image data of the plurality of sequential DSA images.

The color allocation unit generates a color map in which a color in accordance with the parameter value is allocated per pixel corresponding to the same region of the object.

The time phase image generation unit generates color image data of time phase images respectively corresponding to a plurality of time phases, by reflecting information in accordance with pixel values of the DSA images to each pixel of the color map.

(2) In another embodiment, an X-ray diagnostic apparatus includes an X-ray imaging unit and the image analysis device of the above (1).

The X-ray imaging unit generates projection data of X-ray images by detecting X-rays passing through an object before and after administration of a contrast agent, and generates image data of a plurality of sequential DSA images of the object on the basis of each subtraction between an X-ray image before administration of the contrast agent and each of sequential X-ray images after administration of the contrast agent.

The image analysis device acquires a parameter value per pixel, on the basis of time variation of pixel values per pixel corresponding to the same region of the object in the image data of the sequential DSA images, generates a color map in which a color in accordance with the parameter value is allocated per pixel, and generates color image data of time phase images respectively corresponding to a plurality of time phases, by reflecting information in accordance with pixel values of the DSA images to each pixel of the color map.

In the following, embodiments of the present invention will be described with reference to the accompanying drawings. Note that the same reference numbers are given for identical components in each figure, and overlapping explanation is abbreviated.

<Structure of the Present Embodiment>

Figure 1:
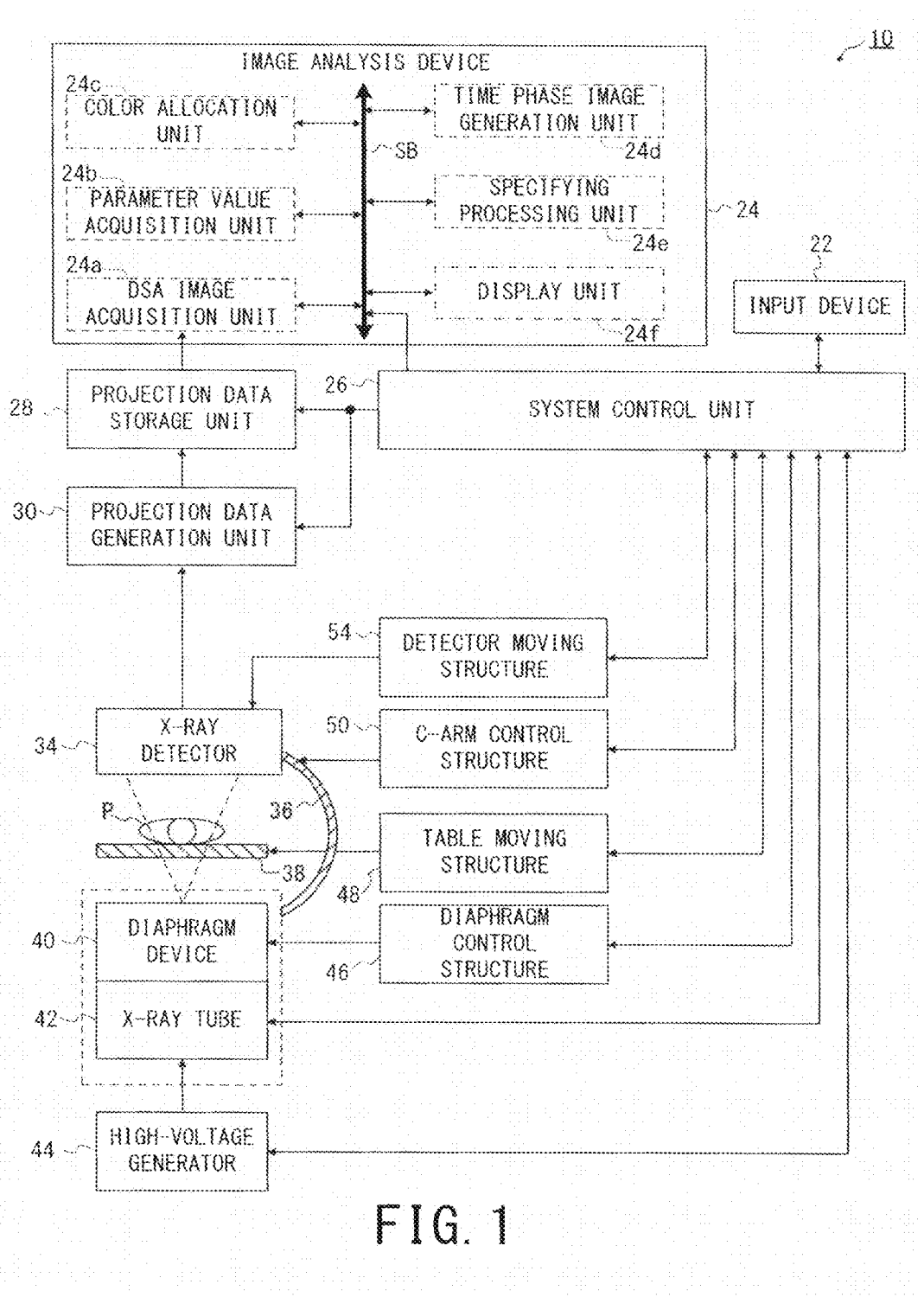
FIG. 1 is a block diagram showing an example of the structure of the X-ray diagnostic apparatus of the present embodiment.

FIG. 1 is a block diagram showing an example of the structure of the X-ray diagnostic apparatus 10 of the present embodiment. As shown in FIG. 1, the X-ray diagnostic apparatus 10 includes an input device 22, an image analysis device 24, a system control unit 26, a projection data storage unit 28, a projection data generation unit 30, an X-ray detector 34, a C-arm 36, a table 38, a diaphragm device 40, an X-ray tube 42, a high-voltage generator 44, a diaphragm control structure 46, a table moving structure 48, a C-arm control structure 50, and a detector moving structure 54.

Because the main characteristics of the X-ray diagnostic apparatus 10 are the functions of the image analysis device 24, the functions of the other components are simply explained as follows and then the functions of the image analysis device 24 will be explained in detail.

An object P is loaded on the table 38.

The C-arm 36 is an arm holding the X-ray tube 42, the diaphragm device 40 and the X-ray detector 34. By this C-arm 36, the X-ray tube 42 and the diaphragm device 40 are disposed to face the X-ray detector 34 with the object P interposed therebetween.

The high-voltage generator 44 generates high voltage and supplies the generated high voltage to the X-ray tube 42.

The X-ray tube 42 generates X-rays by using the high voltage supplied from the high-voltage generator 44.

The diaphragm device 40 narrows down the generated X-rays so as to selectively irradiate the imaging region of the object P, by sliding a plurality of diaphragm blades, for example.

The diaphragm control structure 46 controls irradiation range of X-rays by adjusting degree of opening of diaphragm blades of the diaphragm device 40.

The X-ray detector 34 converts the X-rays passing through the object P by using many X-ray detection elements arrayed in a matrix into electric signals as an example, accumulates the electric signals, and inputs the accumulated electric signals into the projection data generation unit 30.

The projection data generation unit 30 generates projection data by using the electric signals inputted from the X-ray detector 34, and makes the projection data storage unit 28 store the generated projection data. The projection data are, for example, image data of an X-ray image in which each pixel has one pixel value, and each pixel value of the projection data reflects X-ray transmissivity of the imaging region of the object.

As an example here, it is assumed that the projection data generation unit 30 also generates image data of the DSA images on the basis of the projection data and makes the projection data storage unit 28 store the image data of the DSA images.

However, as an alternative structure, a DSA image acquisition unit 24a of the image analysis device 24 may acquire the projection data of X-ray images and generate the image data of the DSA images on the basis of the acquired projection data.

The input device 22 includes a keyboard, a mouse, buttons and so on for a user to input various commands such as imaging conditions and image processing conditions. The input device 22 transfers the inputted contents to the system control unit 26.

The system control unit 26 controls the entirety of the X-ray diagnostic apparatus 10 as to setting imaging conditions, imaging operation and display processing.

Next, each component of the image analysis device 24 will be explained.

The image analysis device 24 includes a system bus SB, the DSA image acquisition unit 24a, a parameter value acquisition unit 24b, a color allocation unit 24c, a time phase image generation unit 24d, a specifying processing unit 24e and a display unit 24f.

The system bus SB is a communication wiring that electrically interconnects the respective components of the image analysis device 24.

The DSA image acquisition unit 24a acquires, from the projection data storage unit 28, the image data of the plurality of sequential DSA images obtained by performing imaging on the same object before and after administration of the contrast agent.

The parameter value acquisition unit 24b acquires parameter values per pixel for parametric imaging, on the basis of time variation of pixel values per pixel corresponding to the same region of the object in the image data of each DSA image (see the later-described FIG. 2).

The above parametric imaging is, for example, processing of forming a color image or gray-scale image from a single parameter or a plurality of parameters. In a broad sense, the parametric imaging includes the projection data of X-ray images generated by the projection data generation unit 30.

This is because the pixel value of each pixel in the case of the projection data of X-ray images indicates a value of X-ray transmissivity as a parameter.

In a narrow sense, the parametric imaging means processing of calculating parameter values except X-ray transmissivity per pixel on the basis of the projection data of X-ray images so as to form a color image. In the present embodiment, the parametric imaging in the narrow sense will be explained from FIG. 2. In addition, in the following explanation, images generated by the parametric imaging in the narrow sense are defined as parametric images.

The color allocation unit 24c generates the image data of parametric images (i.e. the color map) in such a manner that (a) a color in accordance with the parameter value is allocated per pixel corresponding to the same region of the object P and (b) chromatic colors are allocated to a plurality of pixels.

The image data of parametric images are, for example, image data in which each pixel has three pixel values respectively corresponding to the three primary colors of red, green and blue. As an example here, it is assumed that image data of one parametric image is generated for one set of a series of sequential DSA images.

The time phase image generation unit 24d generates color image data of a plurality of parametric time phase images respectively corresponding to a plurality of time phases, by performing color conversion per pixel of one parametric image. As to details of the parametric time phase images, it will be explained later. In addition, the above "a plurality of time phases" means, for example, the time phases of the respective DSA images that are production source of the parametric image.

The specifying processing unit 24e specifies a region with changed bloodstream amount, on the basis of subtraction between each parametric image before operation and each parametric image after the operation. The above "region with changed bloodstream amount" means a bloodstream improving region in the case of the vasodilation operation and means a bloodstream occluded region in the case of the vascular embolus operation, for example.

The display unit (monitor) 24f displays GUI (Graphical User Interface) for receiving commands from a user via the input device 22 and X-ray images. In addition, as one of the main characteristics of the present embodiment, the display unit 24f performs moving picture display of each color image data of the plurality of images respectively corresponding to a plurality of time phase during which the above region with changed bloodstream amount can be distinguished.

Hereinafter, the functions of the image analysis device 24 including generation of the parametric images and extraction of the region with changed bloodstream amount will be explained in detail with reference to FIG. 2 to FIG. 6.

Figure 2:
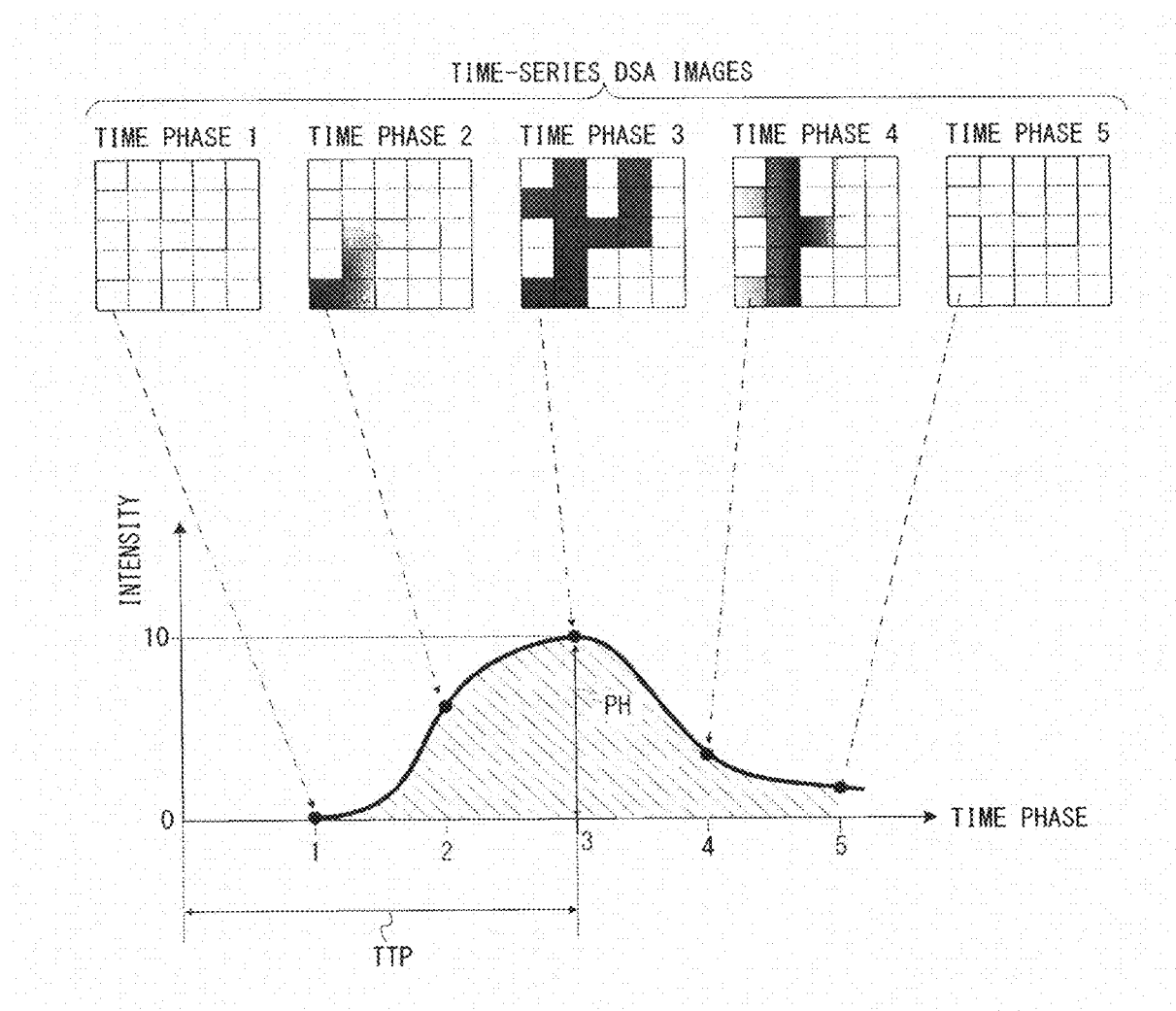
FIG. 2 is a schematic diagram showing a calculating method of time variation of concentration of the contrast medium, as an example of acquiring parameter values in the generation process of the parametric images.

FIG. 2 is a schematic diagram showing a calculating method of time variation of concentration of the contrast medium, as an example of acquiring parameter values in the generation process of the parametric images. The upper part of FIG. 2 indicates the DSA images of the respective time phases, and the lower part of FIG. 2 indicates an example of time variation of concentration of the contrast agent focusing on one pixel.

For example, consider a case where the projection data of six X-ray images of the same imaging region of the same object P are generated by the projection data generation unit 30 in the order of time t=0 before administration of the contrast agent and time t=1, 2, 3, 4, 5 after administration of the contrast agent, under imaging operation of the X-ray diagnostic apparatus 10.

In this case, image data of five DSA images (subtraction images) respectively corresponding to t=1, 2, 3, 4, 5 are obtained by subtracting the X-ray image at t=0 (i.e. the mask image) from each X-ray image after administration of the contrast agent (see the upper part of FIG. 2). Note that, in the upper part of FIG. 2, t=1 is described as time phase 1, and t=2 is described as time phase 2 (the same applies hereinafter).

Here, the parameter value acquisition unit 24b calculates time variation of concentration of the contrast agent per pixel, by calculating time phase variation (from t=1 to t=5) of pixel values per pixel of the same position through the five DSA images.

The lower part of FIG. 2 indicates an example of time variation of the concentration of the contrast agent focusing on the bottom left pixel of each DSA image (in this case, the pixel number of each DSA image is five lines times five columns). In the lower part of FIG. 2, the vertical axis indicates concentration of the contrast agent (intensity of contrast agent), and the horizontal axis indicates time phase (elapsed time t).

More specifically, because the X-ray absorption rate of the contrast agent is higher than that of human tissues, exposure dose of an X-ray detection element corresponding to the position of the object P, where the concentration of the contrast agent is high, becomes lower, and the contrast agent is darkly projected in an X-ray image more than its surrounding areas. Because each pixel value of each DSA image is a difference value from the pixel value of the same position of the mask image (before administration of the contrast agent), if the pixel of the same position is focused on and appropriate processing such as sign inversion is performed on time phase variation of the pixel value of this pixel, the result becomes equivalent to time variation of the concentration of the contrast agent.

The parameter value acquisition unit 24b acquires, for example, at least one of the following three parameters for each pixel, on the basis of the time variation of the concentration of the contrast agent calculated in the above manner.

Firstly, it is TTP (Time To Peak), and TTP indicates at which time phase the concentration of the contrast agent reaches the peak. In the example of the above bottom left pixel, because the concentration of the contrast agent reaches the peak at time phase 3, 3 is given as a parameter value.

Secondly, it is PH (Peak Height), and PH indicates the peak value of the concentration of the contrast agent. In the example of the above bottom left pixel, it is the value of the vertical axis at time phase 3. Note that, the range of the values of the vertical axis can be arbitrarily set in accordance with dynamic range, for example.

Thirdly, it is AUC (Area Under Curve), and AUC indicates a time integration value of the concentration of the contrast agent from the first time phase to the final time phase of the DSA images. In the example of the above bottom left pixel, AUC corresponds to square measure of the diagonally right down shadow region in the lower part of FIG. 2.

The parameter value acquisition unit 24b calculates at least one of the above three parameters for all of the other pixels, by similarly calculating the time variation of the concentration of the contrast agent.

Figure 3:
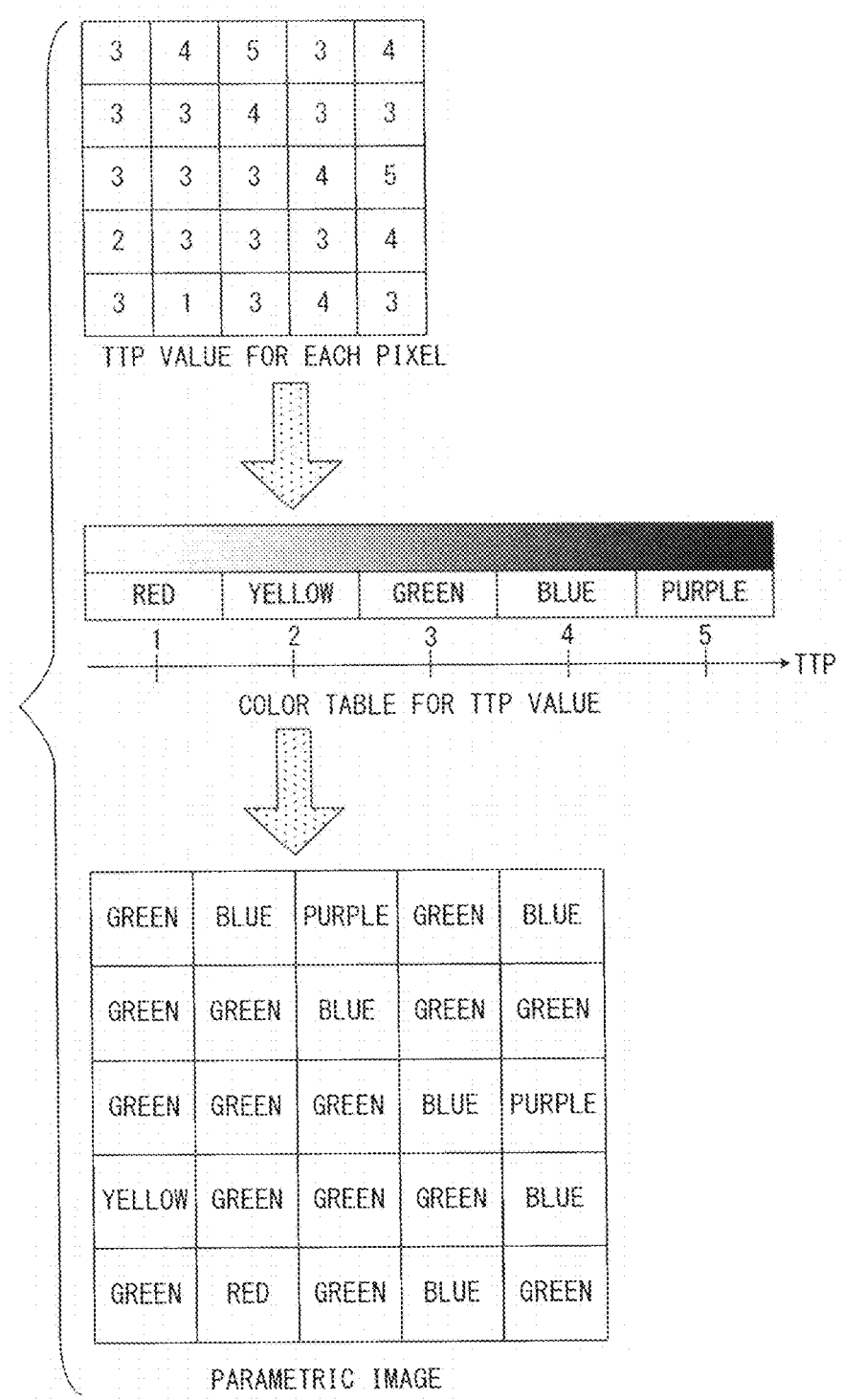
FIG. 3 is a schematic diagram showing an example of generation methods of the parametric images whose parameter is TTP.

FIG. 3 is a schematic diagram showing an example of the generation methods of the parametric images whose parameter is TTP. The upper part of FIG. 3 shows an example of TTP values calculated per pixel of the same position through a plurality of the DSA images, assuming that the pixel number is 5×5, for example.

The middle part of FIG. 3 shows an example of a color table for TTP stored in the color allocation unit 24c. As an example in FIG. 3, red is allocated to pixels whose TTP values are 1, yellow is allocated to pixels whose TTP values are 2, green is allocated to pixels whose TTP values are 3, blue is allocated to pixels whose TTP values are 4, and purple is allocated to pixels whose TTP values are 5.

Although allocation method of color is arbitrary, it is preferable to allocate colors so as to include chromatic colors. This is because it is difficult to distinguish a blood vessel part from its surrounding areas in gray-scale display.

Although three primary colors of red, green and blue are used in the above example of color allocation, this is only an example. For example, color allocation may be performed so that one of the three pixel values of red, green and blue of each pixel becomes always zero. Alternatively, color allocation may be performed so that two of the three pixel values of red, green and blue of each pixel become always zero.

Although the color table is indicated by a gray-scale horizontal bar in FIG. 3 for reasons of expediency, actually color tables may be stored as color bars of chromatic colors.

Alternatively, the color allocation unit 24c may store color tables as table data in which a set of the respective three values of the three primary colors of red, green and blue is indicated in predetermined bit number for each TTP value. For example, in the case of 8 bits, (255, 0, 0) is allocated as each value of red, green and blue for TTP=1.

The lower part of FIG. 3 indicates the color of each pixel defined by the color table in the middle part of FIG. 3 and the TTP value of each pixel in the upper part of FIG. 3. That is, the parametric image of TTP is an image in which the color of each pixel is displayed so as to accord with the color shown in the lower part of FIG. 3.

Note that, the color allocation unit 24c also stores color tables for other parameters such as the color table for AUC and the color table for PH. Although the parametric image is generated by using TTP as a parameter in the above example, the parametric image may be generated by using the aforementioned AUC or PH as a parameter. In addition, the types of parameters are not limited to TTP, AUC or PH. For example, an average value of rising inclination up to the peak in the concentration of the contrast agent may be alternatively used as a parameter.

As just described in FIG. 2 and FIG. 3, one parametric image is generated for a plurality of sequential DSA images by the parameter value acquisition unit 24b and the color allocation unit 24c.

Next, as one of the characteristics of the present embodiment, the time phase image generation unit 24d generates color image data of a plurality of time phase images respectively corresponding to the plurality of sequential DSA images, from one parametric image. In the following explanation, each of the sequential color images generated from one parametric image is referred to as "a parametric time phase image".

Figure 4:
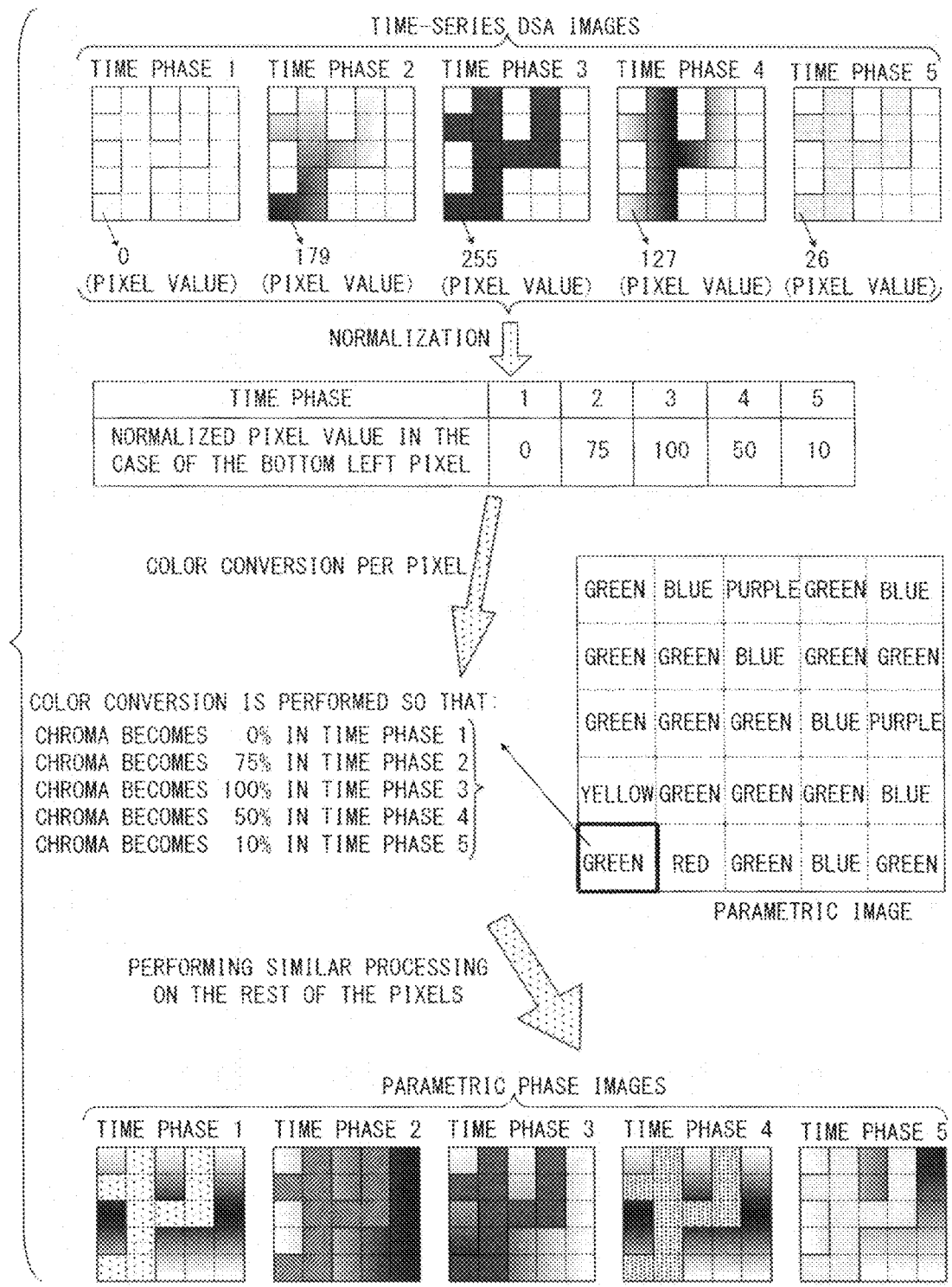
FIG. 4 is a schematic diagram showing the first example of the method of generating the parametric time phase images conducted by the time phase image generation unit, in a step-by-step manner.

FIG. 4 is a schematic diagram showing the first example of the methods of generating the parametric time phase images conducted by the time phase image generation unit 24d in a step-by-step manner.

The uppermost part of FIG. 4 indicates five sequential DSA images shown in FIG. 2. In the example of the uppermost part of FIG. 4, the sequential pixel values of the bottom left pixel through the respective DSA images are 0, 179, 255, 127, 26 from time phase 1 to time phase 5 in order, and the maximum value of them is 255 at time phase 3.

If the above sequential pixel values are normalized on the basis of the maximum pixel value, they become 0%, 75%, 100%, 50%, 10% from time phase 1 to time phase 5 in order (see the second uppermost part of FIG. 4).

Here, in the aforementioned example, the color allocated to the bottom left pixel in the parametric image whose parameter is TTP is green (see the third uppermost part of FIG. 4).

As an example here, the time phase image generation unit 24d performs color conversion on the color of the bottom left pixel of the parametric image, so that the color conversion depends on each pixel value of the pixel of the same position (i.e. bottom left pixel) in the sequential DSA images.

That is, a known color conversion processing is performed on the bottom left pixel of the parametric image, in such a manner that chroma becomes 0%, which is the normalized pixel value of the bottom left pixel of the DSA image at time phase 1. Thereby, the color after this color conversion processing becomes the color of the bottom left pixel of the parametric time phase image at time phase 1.

Similarly, the color conversion processing is performed on the bottom left pixel of the parametric image in such a manner that chroma becomes 75% (which is the normalized pixel value of the bottom left pixel of the DSA image at time phase 2), and the color subjected to this color conversion processing becomes the color of the bottom left pixel of the parametric time phase image at time phase 2.

Similarly, the color conversion processing is performed on the bottom left pixel of the parametric image in such a manner that chroma becomes 100% (which is the normalized pixel value of the bottom left pixel of the DSA image at time phase 3), and the color subjected to this color conversion processing becomes the color of the bottom left pixel of the parametric time phase image at time phase 3.

Similarly, the color conversion processing is performed on the bottom left pixel of the parametric image in such a manner that chroma becomes 50% (which is the normalized pixel value of the bottom left pixel of the DSA image at time phase 4), and the color subjected to this color conversion processing becomes the color of the bottom left pixel of the parametric time phase image at time phase 4.

Similarly, the color conversion processing is performed on the bottom left pixel of the parametric image in such a manner that chroma becomes 10% (which is the normalized pixel value of the bottom left pixel of the DSA image at time phase 5), and the color subjected to this color conversion processing becomes the color of the bottom left pixel of the parametric time phase image at time phase 5.

Note that, because the color of the bottom left pixel of the parametric image is indicated by red=0, green=255 and blue=0 under 8-bit notation of the three primary colors and the chroma of this pixel is originally 100% in the above example, the color of the bottom left pixel of the parametric time phase image at time phase 3 is the same as the color of the bottom left pixel of the parametric image.

Thereby, each color of the bottom left pixel of the respective parametric time phase images from time phase 1 to time phase 5 are determined. As to other pixels, the respective colors of every pixel of the parametric time phase images from time phase 1 to time phase 5 are determined by performing the color conversion processing in the way similar to the above manner. In this manner, the time phase image generation unit 24d generates the color image data of each of the parametric time phase images from time phase 1 to time phase 5.

Note that, the time phase image generation unit 24d may generate the color image data of the parametric time phase images from time phase 1 to time phase 5 by similarly changing luminosity instead of changing chroma. That is, color conversion processing is performed on the color of the bottom left pixel of the parametric image in such a manner that luminosity becomes 0%, 75%, 100%, 50% and 10%, and each color subjected to this color conversion processing becomes the color of the bottom left pixel of the parametric time phase images from time phase 1 to time phase 5.

In addition, the time phase image generation unit 24d may generate the color image data of the parametric time phase images from time phase 1 to time phase 5 by similarly changing transmittance instead of changing chroma.

As just described, examples in which the color image data of the respective parametric time phase images from time phase 1 to time phase 5 are generated by performing the color conversion processing so as to change one of chroma, luminosity and transmittance in accordance with the normalized pixel values of the pixel of the same position in the respective DSA images have been explained. However, embodiments of the present invention are not limited to such an aspect.

For example, the color image data of the respective parametric time phase images from time phase 1 to time phase 5 may be generated on the basis of the parametric image (color map) whose parameter is the aforementioned AUC obtained from the time variation of pixel values of the same position in the plurality of the sequential DSA images, in the way similar to the above manner.

Alternatively, the color image data of the respective parametric time phase images from time phase 1 to time phase 5 may be generated on the basis of the parametric image (color map) whose parameter is the aforementioned PH obtained from the time variation of pixel values of the same position in the plurality of the sequential DSA images, in the way similar to the above manner.

Assuming that there are three cases of generation methods of the parametric image as to which parameter is used and there are three cases of the color conversion processing methods as to which of chroma, luminosity and transmittance is changed, at least there are at least nine (obtained by three times three) methods of generating the parametric time phase images in the manner explained with FIG. 4.

However, as mentioned before, aside from TTP, AUC and PH, there are other parameters to be used for generating the parametric image such as the rising inclination of the time variation curve of the concentration of the contrast agent. In addition, the color conversion processing may be performed in accordance with the normalized pixel value of each pixel of the same position of each DSA image in such a manner that two of chroma, luminosity and transmittance change. Alternatively, the color conversion processing may be performed in accordance with the normalized pixel value of each pixel of the same position of each DSA image in such a manner that all of the chroma, luminosity and transmittance change.

Considering these variations, there are twenty or more than twenty methods of generating the parametric time phase images in the manner explained in FIG. 4.

By displaying each of the parametric time phase images generated in the above manner from time phase 1 to time phase 5 in time-series order, moving picture display can be achieved.

Figure 5:
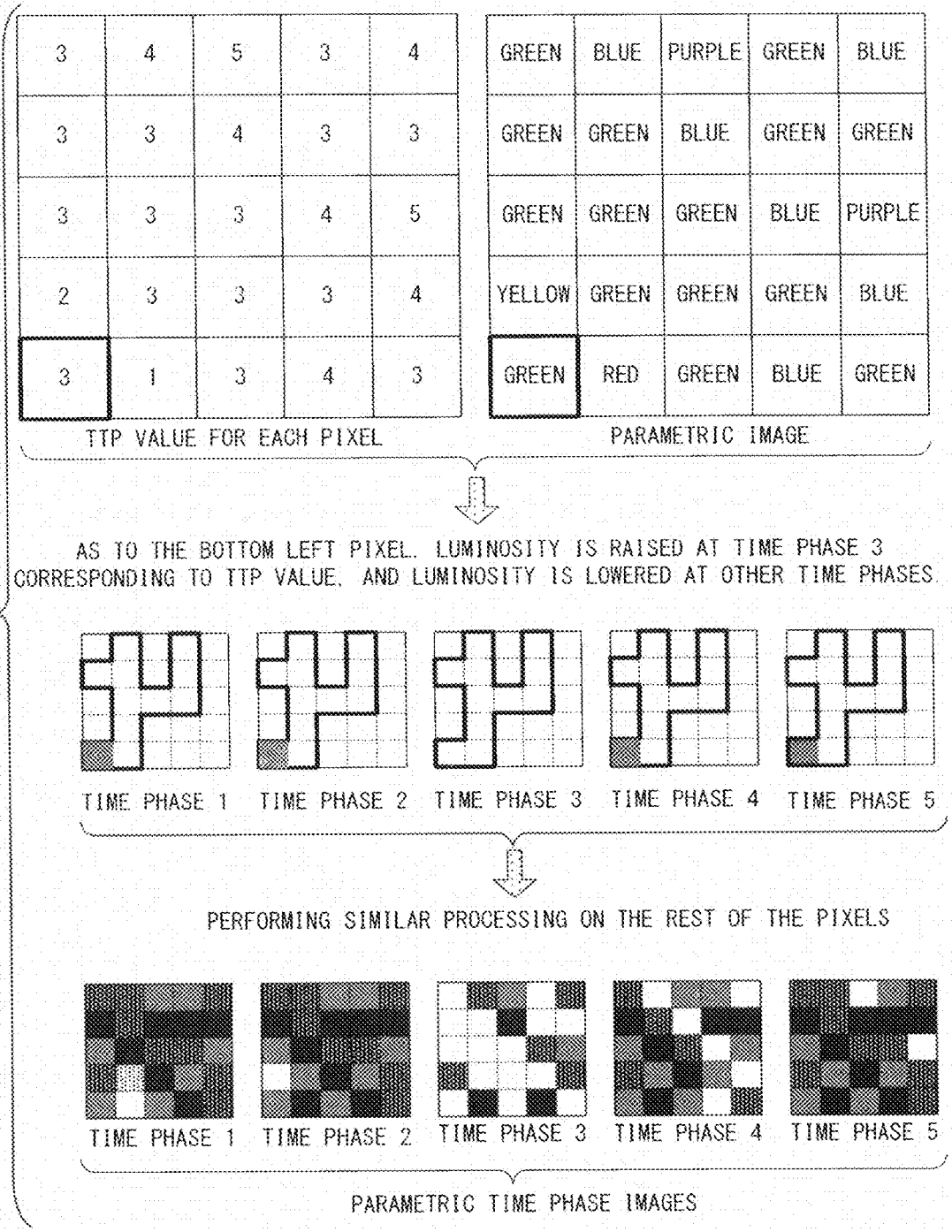
FIG. 5 is a schematic diagram showing the second example of the method of generating the parametric time phase images conducted by the time phase image generation unit, in a step-by-step manner.

FIG. 5 is a schematic diagram showing the second example of the methods of generating the parametric time phase images conducted by the time phase image generation unit 24d in a step-by-step manner. In the way similar to FIG. 4, the second example will be explained by focusing on the bottom left pixel through the five sequential DSA images shown in the upper part of FIG. 5.

Because TTP of the bottom left pixel is 3, the bottom left pixel is displayed so as to become a high contrast pixel only in time phase 3 as shown in the middle part of FIG. 5. The above high contrast pixel means a pixel displayed with raised luminosity in a parametric time phase image of a certain time phase.

That is, because the bottom left pixel is not the high contrast pixel in the four parametric time phase images at time phase 1, 2, 4 and 5, the bottom left pixel is displayed with lowered luminosity in the four parametric time phase images at time phase 1, 2, 4 and 5.

More specifically, the color of the bottom left pixel in each of the parametric time phase images at time phase 1, 2, 4 and 5 becomes a color subjected to the color conversion processing that gives a converted color by lowering luminosity of the green color allocated in the parametric image (color map). As to how to lower luminosity, it may give uniform luminosity (over the time phase 1, 2, 4 and 5). Alternatively, this color conversion processing may be performed so that the lower the normalized pixel value (see the second uppermost part of FIG. 4) is, the lower the luminosity of the converted color becomes.

On the other hand, the color of the bottom left pixel of the parametric time phase image at time phase 3 becomes a color subjected to the color conversion processing that gives the converted color by raising luminosity of the green color allocated in the parametric image (color map). Thereby, the respective colors of the bottom left pixel of the parametric time phase images from time phase 1 to time phase 5 are determined.

As shown in the lower part of FIG. 5, the time phase image generation unit 24d calculates colors of all the pixels of the respective parametric time phase images from time phase 1 to time phase 5 by performing the same color conversion processing on the other pixels.

By displaying the parametric time phase images in time-series order so that the high contrast pixels are brightly displayed and the rest pixels are darkly displayed in the above manner, they are made to look like moving picture display. That is, the sequential parametric time phase images, whose color shade is calculated by using TTP, become moving picture reflecting information on arrival time of the contrast agent.

Note that, though examples in which the pixel number of each of the DSA images, the parametric images and the parametric time phase images is 25 have been explained in order to avoid complication, the pixel number of these images may be equal to or more than twenty-six, or equal to or less than twenty-four. In addition, as to the three sorts of images including the DSA images, the parametric images and the parametric time phase images, their pixel number in height and width does not need to be uniform.

If the pixel number of the DSA images is extremely large, the pixel number of each of the parametric image and the parametric time phase images may be thinned out so as to become a half of the pixel number of the DSA images in height and become a half of the pixel number of the DSA images in width, for example.

In addition, though examples of five time phases have been explained for simplifying the explanation, the number of time phases may be six or more.

Figure 6:
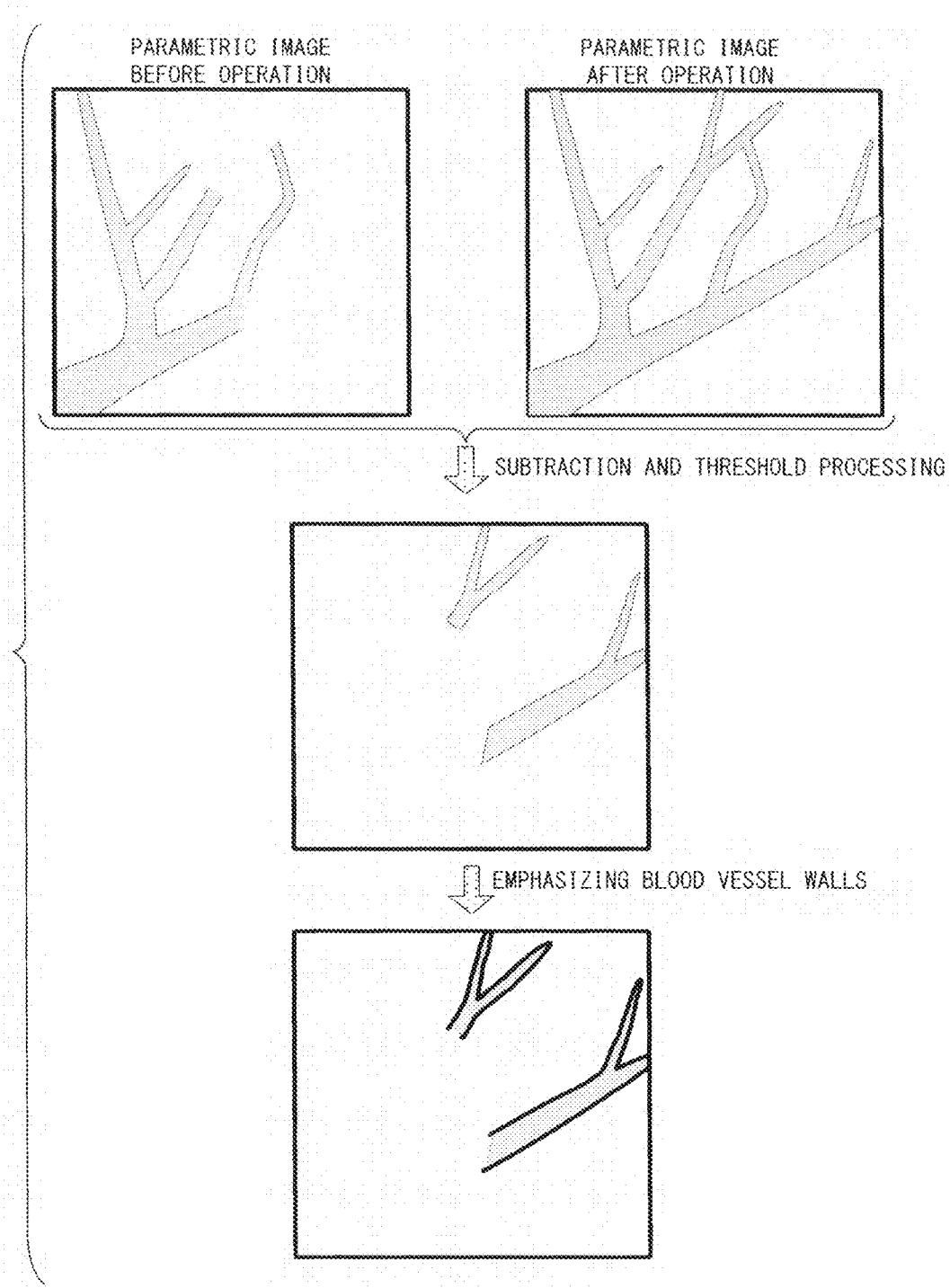
FIG. 6 is a schematic diagram showing the judging method of a bloodstream improving region after the vasodilation operation or the like conducted by the specifying processing unit, in a stepwise fashion.

FIG. 6 is a schematic diagram showing the judging method of a bloodstream improving region after the vasodilation operation or the like conducted by the specifying processing unit 24e, in a stepwise fashion.

In the way similar to the aforementioned examples, consider a case where five pre-operative DSA images 1, 2, 3, 4 and 5 are generated from the same imaging region of the object P before the operation, and five post-operative DSA images 1', 2', 3', 4' and 5' are generated from the same imaging region of the same object after the operation.

In this case, the parameter value acquisition unit 24b and the color allocation unit 24c generate one pre-operative parametric image from the pre-operative DSA images 1 to 5 by using PH as a parameter in the same manner as above (see the upper left part of FIG. 6). Similarly, the parameter value acquisition unit 24b and the color allocation unit 24c generate one post-operative parametric image from the post-operative DSA images 1' to 5' by using PH as a parameter in the same manner as above (see the upper right part of FIG. 6).

Next, the specifying processing unit 24e generates a subtraction image by subtracting each pixel value of the pre-operative parametric image from each pixel value of the post-operative parametric image, so that the subtraction is performed between the two pixels of the same position before and after the operation.

The specifying processing unit 24e extracts a pixel region whose pixel value is equal to or larger than a threshold value in this subtraction image, as the bloodstream improving region (see the middle part of FIG. 6).

Note that, the bloodstream improving region can be extracted by (a) generating the pre-operative parametric image and the post-operative parametric image by using AUC as a parameter instead of PH and (b) performing the threshold processing on the subtraction image in the same way as above.

Moreover, the specifying processing unit 24e generates vessel wall emphasis image data in which contour of blood vessels (vessel walls) in the bloodstream improving region is emphasized.

More specifically, for example, the specifying processing unit 24e can generate the vessel wall emphasis image data by applying contour emphasis processing such as a Laplacian filter to the bloodstream improving region extracted from the above subtraction image (see the bottom part of FIG. 6).

On the other hand, the bloodstream occluded region after the vascular embolus operation or the like are similarly judged except that the subtracted side is reversed in the generation processing of the subtraction image. That is, the specifying processing unit 24e generates the subtraction image by subtracting each pixel value of the post-operative parametric image from each pixel value of the pre-operative parametric image, and calculates the pixel region whose pixel value is equal to or higher than a threshold value as the bloodstream occluded region.

<Display Method of the Present Embodiment>

Figure 7:
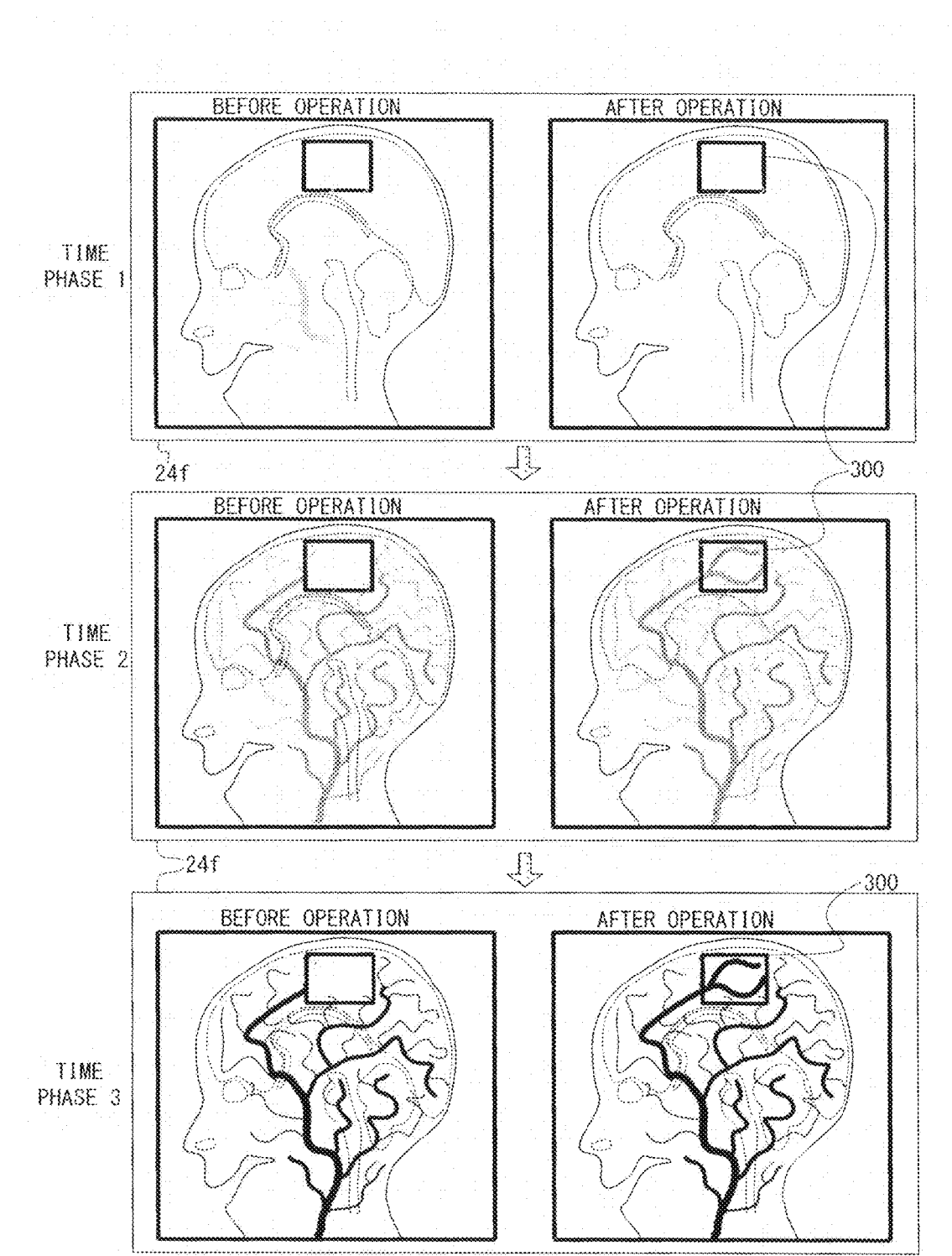
FIG. 7 is a schematic diagram showing an example of distinguishably displaying the bloodstream improving region by surrounding it with a frame, in moving picture display of the parametric time phase images.

FIG. 7 is a schematic diagram showing an example of distinguishably displaying the bloodstream improving region by surrounding it with a frame, in moving picture display of the parametric time phase images.

As an example here, the respective parametric time phase images corresponding to the respective time phases of the pre-operative DSA images are displayed in time-series order in the left side of the screen of the display unit 24f and the respective parametric time phase images corresponding to the respective time phases of the post-operative DSA images are displayed in time-series order in the right side of the screen. The same holds true for the following FIG. 8 to FIG. 10.

Figure 8:
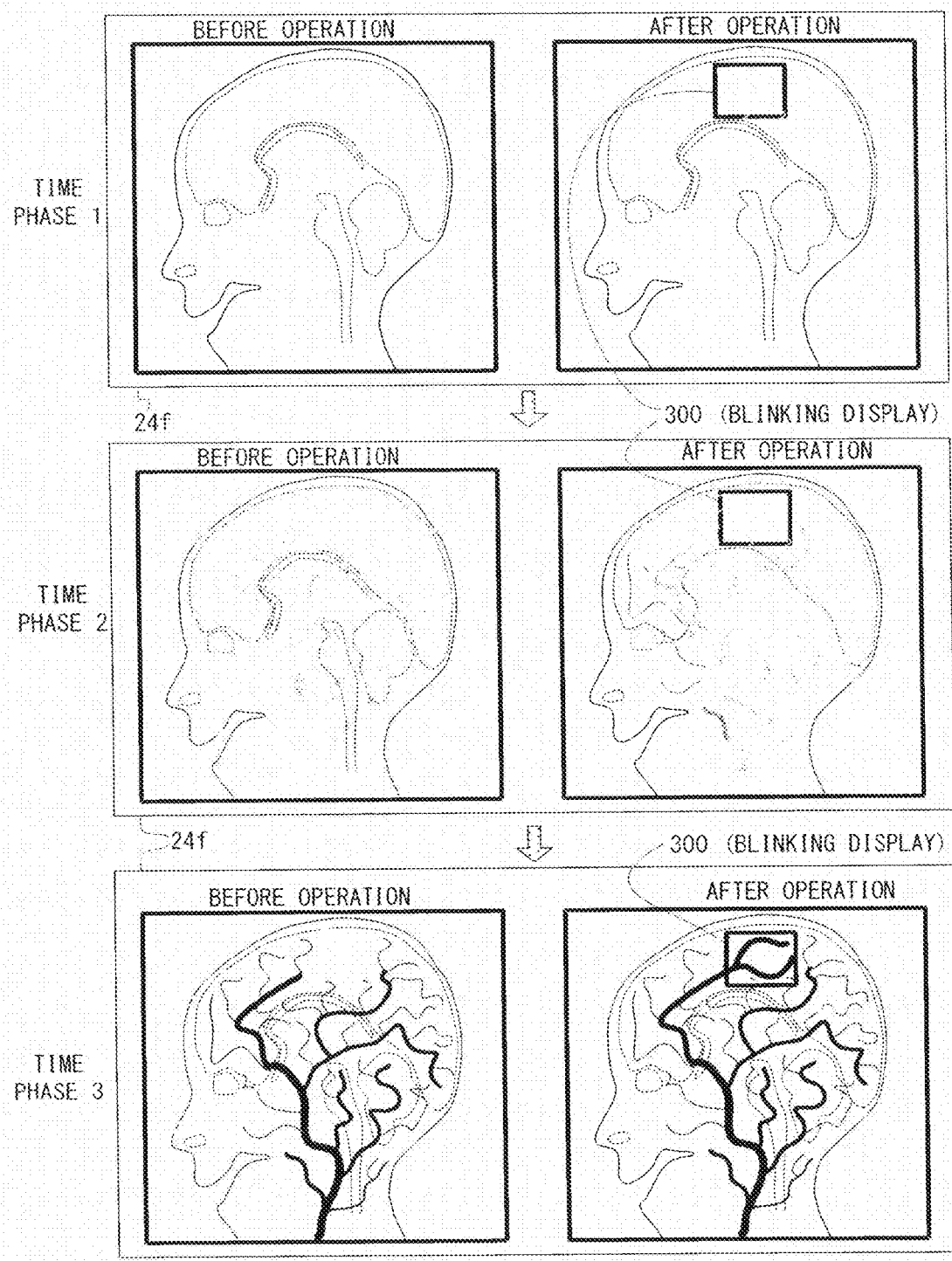
FIG. 8 is a schematic diagram showing an example of distinguishably displaying the bloodstream improving region by blinking it, in moving picture display of the parametric time phase images.
Figure 9:
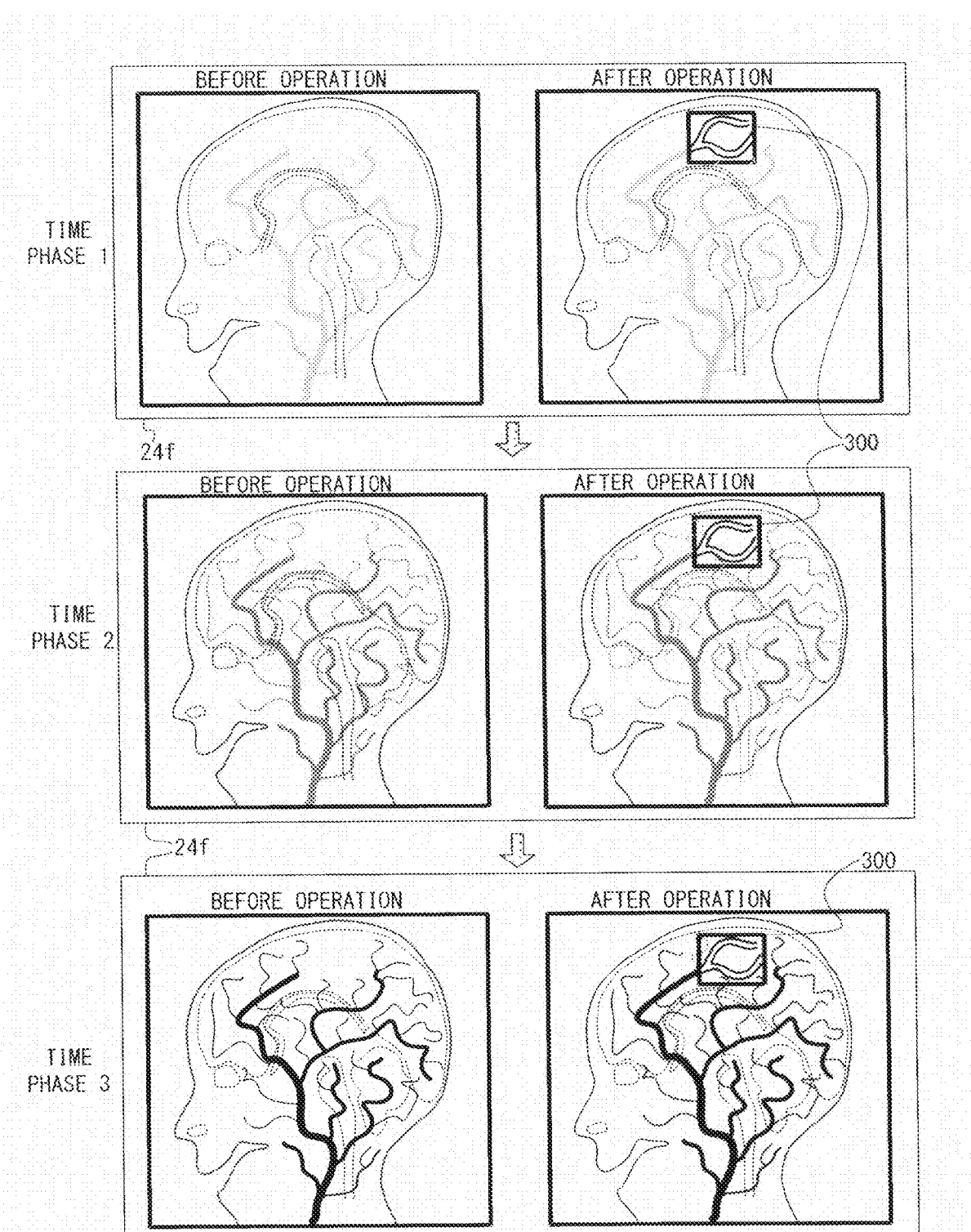
FIG. 9 is a schematic diagram showing an example of a highlighted blood vessel wall extracted by the specifying processing unit, in moving picture display of the parametric time phase images.
Figure 10:
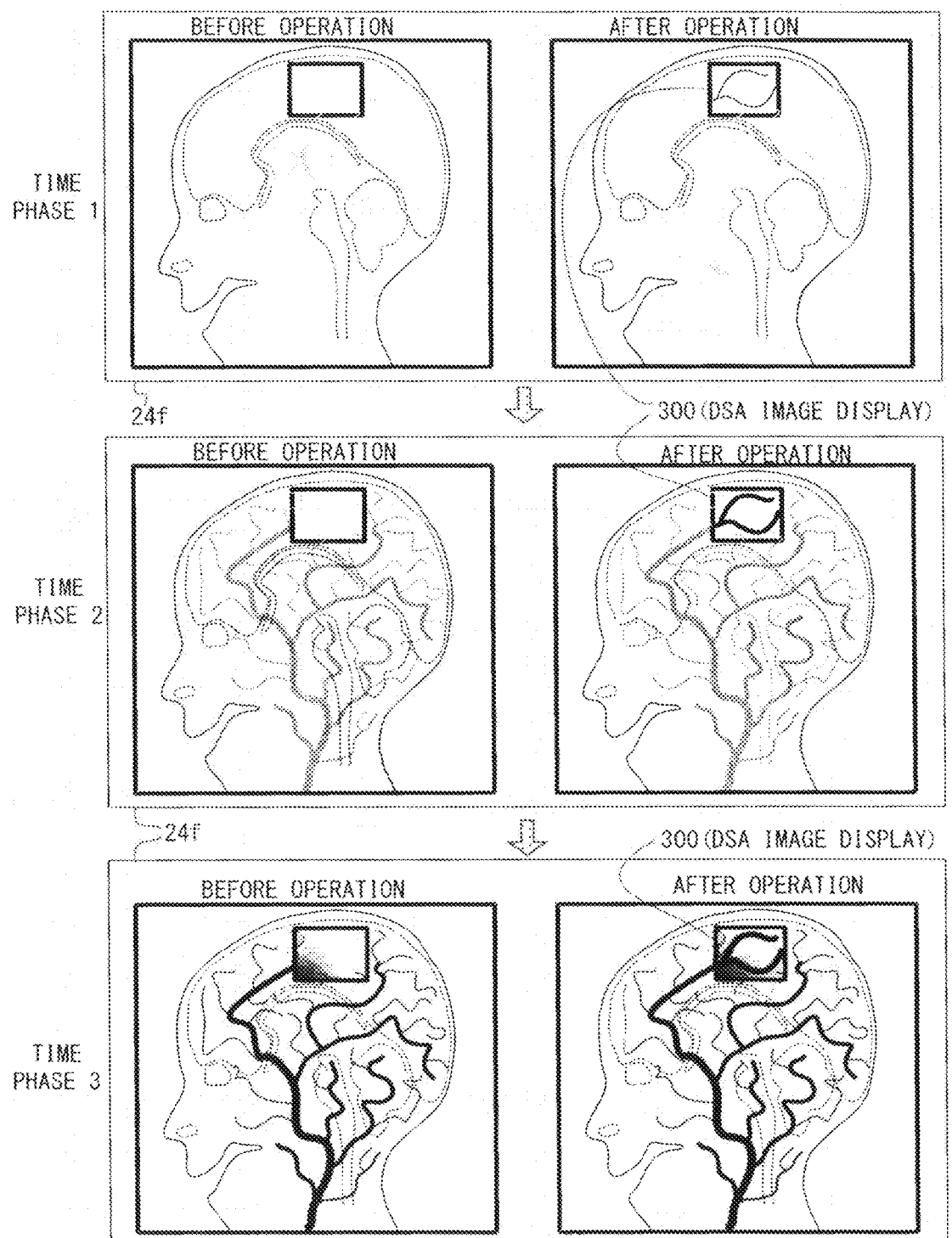
FIG. 10 is a schematic diagram showing an example of displaying only the bloodstream improving region by using the DSA images as a moving gray-scale picture and displaying the rest of the regions in color by using the parametric time phase images, in moving picture display of the parametric time phase images.

As shown in FIG. 7, the display unit 24f can distinguishably display the bloodstream improving region extracted by the specifying processing unit 24e as ROI (Region of Interest) 300 surrounded with a rectangular frame, in moving picture display of both of the pre-operative parametric time phase images and the post-operative parametric time phase images Note that, though images up to only time phase 3 are depicted in FIG. 7 in order to avoid complication, actually images on and after time phase 4 are also displayed (the same holds true for the following FIG. 8 to FIG. 10).

In addition, though the pre-operative parametric time phase images are displayed as moving pictures for comparison, only the post-operative parametric time phase images may be displayed so as to differentiate the bloodstream improving region (the same holds true for the following FIG. 8 to FIG. 10).

In addition, though the same pixel region as the post-operative bloodstream improving region is distinguishably displayed in the moving picture of pre-operative parametric time phase images by surrounding it with a frame in FIG. 7, the bloodstream improving region may be distinguishably displayed only in the post-operative moving picture like the next FIG. 8.

FIG. 8 is a schematic diagram showing an example of distinguishably displaying the bloodstream improving region by blinking it, in moving picture display of the parametric time phase images.

In the example of FIG. 8, the display unit 24f distinguishably displays the bloodstream improving region as ROI 300 by blinking the bloodstream improving region. As to blinking display, for example, luminosity of the pixels of ROI 300 may be alternately (intermittently) raised and lowered. Alternatively, if the number of time phases is sufficiently large, ROI 300 may be displayed with lowered luminosity only in even-numbered time phases like the example of FIG. 8.

FIG. 9 is a schematic diagram showing an example of a highlighted blood vessel wall extracted by the specifying processing unit 24e, in moving picture display of the parametric time phase images. As shown in FIG. 9, the display unit 24f can highlight the blood vessel wall extracted by the specifying processing unit 24e by using, for example, a bold line in ROI (the bloodstream improving region) 300, while distinguishably displaying this ROI 300 by surrounding it with a frame in each of the post-operative parametric time phase images.

FIG. 10 is a schematic diagram showing an example of displaying only the bloodstream improving region by using the DSA images as a moving gray-scale picture and displaying the rest of the regions in color by using the parametric time phase images, in moving picture display of the parametric time phase images.

As mentioned above, when a plurality of parametric time phase images are generated so as to correspond to the respective time phases of a plurality of DSA images, the display unit 24f can perform moving picture display of the parametric time phase images in such a manner that only the ROI (bloodstream improving region) 300 is substituted by the same region of the DSA image of the same time phase.

More specifically, each pixel has pixel values of the three primary colors including red, green and blue in the parametric time phase images, for example. On the other hand, each pixel of the DSA images has only one pixel value. This is because each pixel value of the DSA images corresponds to difference in X-ray transmissivity between a pixel value of a certain time phase after administration of the contrast agent and a pixel value of the mask image.

Thus, because the ROI 300 displayed by using pixel values of the DSA images does not have data of chromatic color, it is displayed with a gray-scale. However, because the rest regions are chromatically displayed, the ROI 300 displayed with a gray-scale becomes a distinguishable display aspect.

Note that, though FIG. 7 to FIG. 10 are indicated by gray-scale schematic diagrams for the sake of expedience, actually they are chromatically displayed except the ROI 300 in FIG. 10 because each of the parametric time phase images are formed by color image data.

In addition, though examples in which the bloodstream improving region is distinguishably displayed have been explained in FIG. 7 to FIG. 10, the same display aspect as FIG. 7 to FIG. 10 can be applied when the bloodstream occluded region after the vascular embolus operation is distinguishably displayed.

<Operation Explanation of the Present Embodiment>

Figure 11:
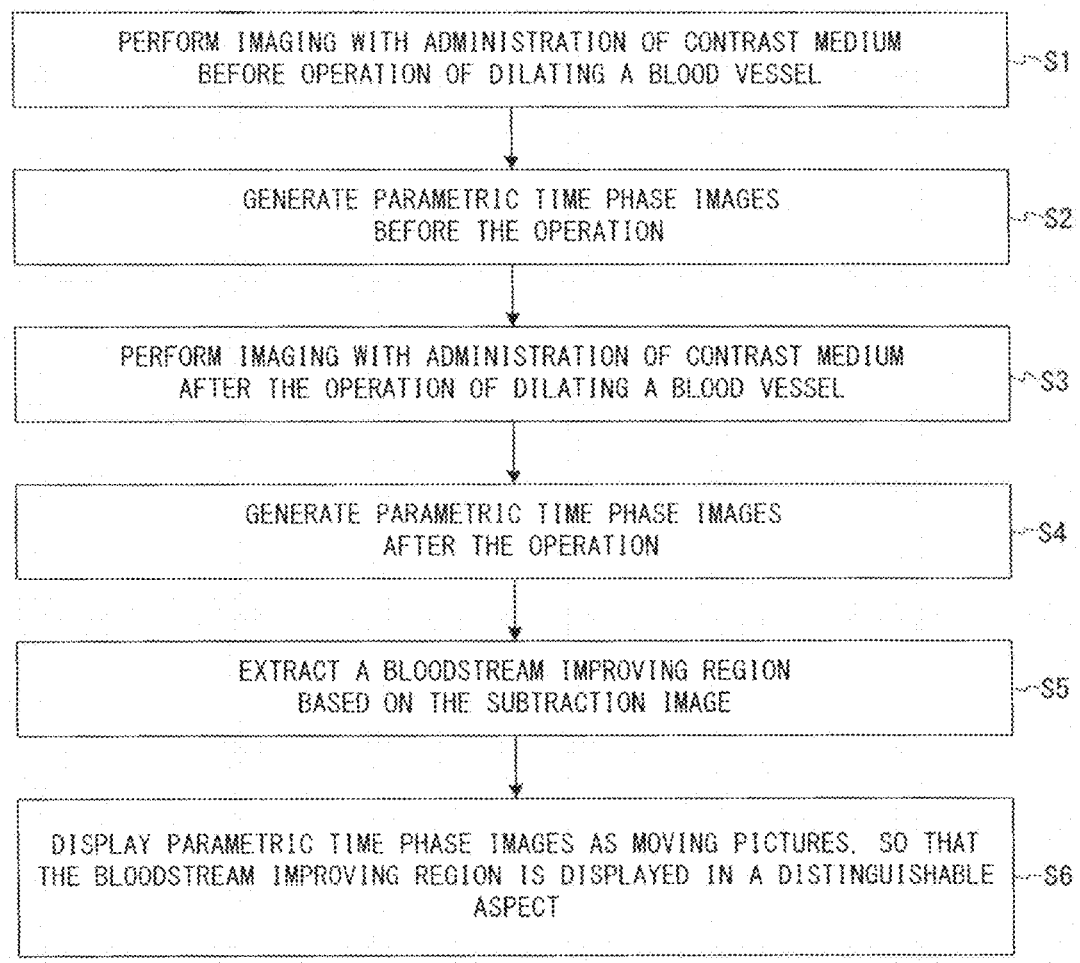
FIG. 11 is a flow chart showing an example of the operation of the X-ray diagnostic apparatus of the present embodiment, when imaging with administration of the contrast agent before and after the vasodilation operation and display of the bloodstream improving region are performed.

FIG. 11 is a flow chart showing an example of the operation of the X-ray diagnostic apparatus 10 of the present embodiment, when imaging with administration of contrast agent before and after the vasodilation operation and display of bloodstream improving region are performed.

In the following, according to the step numbers in the flowchart shown in FIG. 11, an operation of the X-ray diagnostic apparatus 10 will be described by referring to the aforementioned FIG. 1 to FIG. 10 as required.

[Step S1] Before the vasodilation operation, the projection data of a plurality of sequential X-ray images for the same region of the object P are generated under known operation. More specifically, the system control unit 26 (see FIG. 1) sets all the imaging conditions of each time phase before and after administration of the contrast agent, on the basis of some of the imaging conditions such as the imaging region, tube current, tube voltage and a pulse width of X-rays inputted via the input device 22. The high-voltage generator 44 supplies high voltage to the X-ray tube 42 in accordance with the control of the system control unit 26, the X-ray tube 42 generates X-rays, and the diaphragm device 40 adjusts the X-ray irradiation range to the object P.

The X-ray detector 34 detects X-rays passing through the object P, converts them into electrical signals, and inputs the electrical signals into the projection data generation unit 30. The projection data generation unit 30 generates the projection data of X-ray images on the basis of the inputted electrical signals, and stores the projection data in the projection data storage unit 28.

In this manner, the projection data of many time phases for the same region of the object P are generated, in such a manner that luminance of each pixel becomes a value in accordance with exposure dose per non-illustrated X-ray detection element of the X-ray detector 34 before and after administration of the contrast agent.

Note that, though a plurality of X-ray images after administration of the contrast agent are necessary so as to correspond to a plurality of time phases, the number of the X-ray image before the contrast agent may be only one.

Moreover, the projection data generation unit 30 generates the image data of the plurality of sequential DSA images for the same region of the object P on the basis of the projection data, and stores the image data of these DSA images in the projection data storage unit 28.

After this, the process proceeds to Step S2.

[Step S2] The DSA image acquisition unit 24a of the image analysis device 24 acquires the image data of the plurality of sequential DSA images from the projection data storage unit 28. The parameter value acquisition unit 24b calculates parameter values per pixel of the same position from the image data of the plurality of sequential DSA images (see FIG. 2).

Note that, as to which of TTP, PH, AUC and so on is used as the parameter value, it may be selected via the input device 22 in Step S1. Alternatively, the parameter value acquisition unit 24b may automatically select the parameter to be used.

Next, the color allocation unit 24c generates the image data of one parametric image for the plurality of sequential DSA images in the manner mentioned before (see FIG. 3).

Next, the time phase image generation unit 24d generates the image data of the plurality of parametric time phase images respectively corresponding to the plurality of (pre-operative) sequential DSA images, in the aforementioned manner. As to this generation method, the first method explained with FIG. 4 and/or the second method explained with FIG. 5 may be used.

After this, the process proceeds to Step S3.

[Step S3] After the vasodilation operation, the projection data of sequential X-ray images for the same imaging region of the same object P as Step S1 are generated, in the way similar to Step S1. Thereby, the projection data of many time phases are generated for the same region of the object P before and after the administration of the contrast agent. Moreover, the projection data generation unit 30 generates the image data of the plurality of sequential DSA images for the same region of the object P in the same way as above, and stores these image data in the projection data storage unit 28.

After this, the process proceeds to Step S4.

[Step S4] In the way similar to Step S3, the image analysis device 24 generates the image data of the plurality of parametric time phase images respectively corresponding to the plurality of post-operative sequential DSA images.

After this, the process proceeds to Step S5.

[Step S5] The specifying processing unit 24e of the image analysis device 24 generates the subtraction image by subtracting each pixel value of the pre-operative parametric image from each pixel value of the post-operative parametric image, and extracts a pixel region whose pixel value is equal to or higher than the threshold value in the subtraction image, as the bloodstream improving region (see FIG. 6). In addition, the specifying processing unit 24e generates the vessel wall emphasis image data in which vessel walls in the bloodstream improving region is emphasized as described previously.

After this, the process proceeds to Step S6.

[Step S6] The display unit 24f of the image analysis device 24 displays the post-operative parametric time phase images in time-series order, in such a manner that the bloodstream improving region extracted in Step S5 is distinguishably displayed. That is, moving picture display is performed. At this time, the pre-operative parametric time phase images may be displayed on one side of the screen and the post-operative parametric time phase images may be displayed on the other side of the screen for comparison like FIG. 7 to FIG. 10.

In addition, as to distinguishable display of the ROI (bloodstream improving region) 300, it may be surrounded by a rectangular frame like FIG. 7, or blinking display may be performed like FIG. 8. Alternatively, blood vessel walls are emphasized in ROI 300 like FIG. 9. Alternatively, only the bloodstream improving region may be displayed as gray-scale moving pictures by using the DSA images and the rest regions may be chromatically displayed by using the parametric time phase images like FIG. 10.

The foregoing is the explanation of the flow of FIG. 11.

Figure 12:
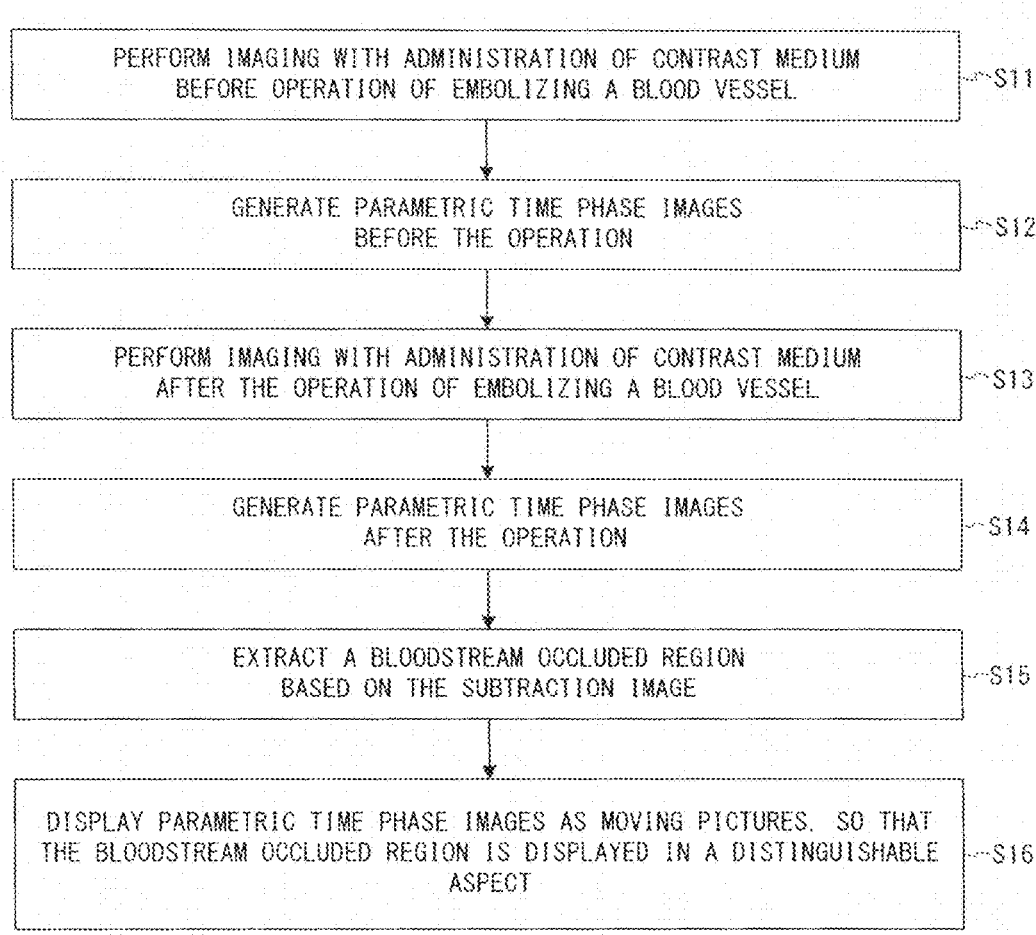
FIG. 12 is a flow chart showing an example of the operation of the X-ray diagnostic apparatus of the present embodiment, when imaging with administration of the contrast agent before and after the vascular embolus operation and display of the bloodstream occluded region are performed.

FIG. 12 is a flow chart showing an example of the operation of the X-ray diagnostic apparatus 10 of the present embodiment, when imaging with administration of the contrast agent before and after the vascular embolus operation and display of the bloodstream occluded region are performed. In the following, according to the step numbers in the flowchart shown in FIG. 12, an operation of the X-ray diagnostic apparatus 10 will be described by referring to the aforementioned FIG. 1 to FIG. 11 as required.

[Step S11] Before vascular embolus operation, the projection data of the plurality of sequential X-ray images before and after administration of the contrast agent and the image data of the plurality of sequential DSA images are generated for the same imaging region of the object P, in the way similar to Step S1 of FIG. 11.

After this, the process proceeds to Step S12.

[Step S12] The image analysis device 24 generates the image data of the parametric time phase images of the respective time phases before the operation, in the way similar to Step S2 of FIG. 11.

After this, the process proceeds to Step S13.

[Step S13] After the vascular embolus operation, the projection data of the plurality of sequential X-ray images before and after administration of the contrast agent and the image data of the plurality of sequential DSA images are generated for the same imaging region of the same object P as Step S11, in the same way as above.

After this, the process proceeds to Step S14.

[Step S14] The image analysis device 24 generates the image data of the parametric time phase images of the respective time phases after the operation, in the same way as above.

After this, the process proceeds to Step S15.

[Step S15] The specifying unit 24e generates the subtraction image by subtracting each pixel value of the post-operative parametric image from each pixel value of the pre-operative parametric image, and extracts a pixel region whose pixel value is equal to or higher than the threshold value in the subtraction image, as the bloodstream occluded region.

After this, the process proceeds to Step S16.

Note that, the processing of emphasizing blood vessel walls is not performed in the flow of FIG. 12 because the effect of the operation is blockage of blood flow.

[Step S16] The display unit 24f time-sequentially displays the post-operative parametric time phase images in such a manner that the bloodstream occluded region extracted in Step S15 is distinguishably displayed, in the way similar to the aforementioned FIG. 7, FIG. 8 and FIG. 10.

The foregoing is the operation explanation of the X-ray diagnostic apparatus 10 of the present embodiment.

<Effects of the Present Embodiment>

In conventional technology, one parametric image is generated before operation or after operation, and the parametric image is displayed as a still picture. In still picture display, it is not necessarily easy to visually judge a bloodstream improving region or a bloodstream improving region indicating the effect of the operation.

Then, in the present embodiment, the parametric time phase images of the plurality of time phases respectively corresponding to the DSA images of the plurality of time phases are generated from one parametric image in accordance with time variation of pixel values.

Furthermore, because the pre-operative parametric time phase images and the post-operative parametric time phase images are respectively displayed as moving pictures, it becomes easier than the conventional technology to visually judge a region with changed bloodstream amount.

Moreover, in the present embodiment, the bloodstream improving region or the bloodstream occluded region is automatically extracted on the basis of the subtraction image between the pre-operative parametric images and the post-operative parametric images.

This extracted bloodstream improving region or bloodstream occluded region is distinguishably displayed in the moving picture display of the parametric time phase images in the manner of FIG. 7 to FIG. 10, for example. Thus, a reader can easily visually judge the bloodstream improving region or the bloodstream improving region indicating the effects of the operation.

By the above epoch-making and innovative technology, oversight of a reader will decrease even if the difference between before and after the operation is small.

On the other hand, in the conventional technology, there was a work burden in finding out a small difference by switching still picture display of the parametric image, moving picture display of the DSA images and still picture display of the DSA image of each time phase. However, the above work burden in the conventional technology becomes unnecessary by the present embodiment.

As a result, user-friendliness is highly improved.

<Supplementary Notes on Embodiments>

[1] In the above embodiment, an example in which the image analysis device 24 is disposed as one component inside the X-ray diagnostic apparatus 10 has been explained. However, embodiments of the present invention are not limited to such an aspect. For example, the image analysis device 24 may be disposed in another modality such as an X-ray CT (Computed Tomography) apparatus or a magnetic resonance imaging apparatus.

As an alternative aspect, the image analysis device 24 may function as an image analysis server connected with PACS (Picture Archiving and Communication System). The above picture archiving and communication system is a system in which image data obtained by modalities such as an X-ray diagnostic apparatus are stored in an image storage server and necessary images are read and displayed in a reference terminal. In this case, the image analysis device 24 may acquire image data of the plurality of sequential DSA images for the same the object P via the picture archiving and communication system, and display the parametric time phase images as moving pictures in such a manner that the region with changed bloodstream amount is distinguishably displayed in the way similar to the above embodiment.

[2] In the above embodiment, examples in which the parametric time phase images respectively corresponding to the respective time phases of all the acquired DSA images are generated and all the generated parametric time phase images are displayed in time-series order have been explained. However, it is not necessarily essential to generate the parametric time phase images so as to respectively correspond to all the time phases of the DSA images.

When the number of the acquired DSA images is considerably large, i.e. the time phase number of the DSA images is considerably large, the time phase number of the parametric time phase images may be thinned out to a degree at which all the generated parametric time phase images gives visually natural moving pictures. For example, when the DSA images of one hundred time phases are acquired, fifty parametric time phase images may be generated by using the fifty DSA images of the even-numbered time phases and these fifty parametric time phase images may be time-sequentially displayed.

[3] In the above embodiment, examples in which the plurality of sequential DSA images are generated on the basis of sequential two-dimensional image data obtained by imaging before and after administration of the contrast agent and the plurality of parametric time phase images respectively corresponding to these DSA images are generated and two-dimensionally displayed as moving pictures have been explained. However, embodiments of the present invention are not limited to such an aspect.

For example, when volume data are sequentially obtained by imaging under an X-ray CT apparatus or a magnetic resonance imaging apparatus, (the parallax images of) the plurality of sequential parametric time phase images may be displayed as moving pictures by a naked eye stereoscopic display device. In this case, the display unit 24f is composed as a naked eye stereoscopic display device, and image data of the plurality of the parallax images are generated per parametric time phase image corresponding to each imaging time.

More specifically, the sequential parametric time phase images 1 to 5 are generated on the basis of the respective pixel value of the central cross-section of volume data in the above manner, for example (as described previously, frame number is not limited to five). Then, depth information is calculated on the basis of pixel values of all the cross-sections of the volume data, and the plurality of the parallax images are generated for each of the parametric time phase images of the plurality of time phases on the basis of the depth information.

If the plurality of the parallax images are generated for each time phase (each imaging time), the parametric time phase images can be three-dimensionally displayed by a naked eye stereoscopic display device. As to methods of generating parallax images and structure of a naked eye stereoscopic display device, for example, conventional technology described in Japanese Patent Application Laid-open (KOKAI) Publication No. 2007-94022 may be used.

[4] In the above embodiment, examples in which (a) a bloodstream improved region or a bloodstream occluded region due to an operation is automatically extracted and (b) the bloodstream improving region or the bloodstream occluded region is displayed in a distinguishable aspect in moving picture display of the parametric time phase images have been explained. However, embodiments of the present invention are not limited to such an aspect.

Extraction processing of the bloodstream improving region or the bloodstream occluded region is not indispensable, and the parametric time phase images may be simply displayed as moving pictures.

As to moving picture display, for example, the parametric time phase images may be displayed with the DSA images of the respective time phase.

More specifically, for example, the DSA images may be sequentially displayed on the right side of the screen of the display unit 24f, and the parametric time phase image corresponding to the time phase of the DSA image currently displayed on the right side of the screen may be displayed on the left side of the screen so as to follow the display on the right side of the screen.

As to moving picture display of the parametric time phase images on the left side of the screen, it is preferable to distinguishably display the bloodstream improving region or the bloodstream occluded region extracted based on the difference from the pre-operative image like the above embodiment.

Alternatively, the post-operative DSA images, the parametric image and the parametric time phase images may be concurrently displayed (in one screen). For example, the respective post-operative DSA images may be displayed in time-series order on the upper part of the screen in the same way as above, the parametric time phase images may be displayed in time-series order on the middle part of the screen in the same way as above, and one post-operative parametric image may be displayed as a still picture on the bottom part of the screen.

[5] In the above embodiment, examples in which (a) the region with changed bloodstream amount is specified on the basis of the subtraction between the pre-operative parametric image and the post-operative parametric image (see FIG. 6) and (b) the region with changed bloodstream amount is distinguishably displayed in moving picture display of the respective parametric time images before and after the operation have been explained (see FIG. 7 to FIG. 10). However, embodiments of the present invention are not limited to such an aspect.

In terms of specifying the region with changed bloodstream amount, it is enough to perform comparison between two time points in the time axis from a time before staring an operation to a time after finishing the operation.

For example, the region with changed bloodstream amount may be identified on the basis of the subtraction between the parametric image obtained from pre-operative sequential DSA images and the parametric image obtained from sequential DSA images in the middle of the operation, and the identified region with changed bloodstream amount may be distinguishably displayed in the same way as mentioned above.

In addition, it is not indispensable to display both of the pre-operative sequential parametric time phase images and the post-operative sequential parametric time phase images.

For example, only the pre-operative sequential parametric time phase images may be generated and sequentially displayed as moving pictures if it is used for diagnosis purposes.

For example, if the region to be cured has already been identified, only the post-operative sequential parametric time phase images may be generated and sequentially displayed as moving pictures in order to confirm the effect of the operation.

[6] Correspondences between terms used in the claims and terms used in the embodiment described above will be described. Note that the correspondences described below are just some of possible interpretations for reference and should not be construed as limiting the present invention.

The image data of the parametric image generated by the color allocation unit 24c are an example of the color map described in the claims.

The image data of the parametric time phase images generated by the time phase image generation unit 24d are an example of the color image data of time phase images described in the claims.

The subtraction image between the pre-operative parametric image and the post-operative parametric image generated by the specifying processing unit 24e is an example of the subtraction map described in the claims.

The bloodstream improving region and the bloodstream occluded region extracted by the specifying processing unit 24e are examples of the region with changed bloodstream amount described in the claims.

The entirety of the system control unit 26, the projection data storage unit 28, the projection data generation unit 30, the X-ray detector 34, the C-arm 36, the table 38, the diaphragm device 40, the X-ray tube 42, the high-voltage generator 44, the diaphragm control structure 46, the table moving structure 48, the C-arm control structure 50 and the detector moving structure 54 that generates the projection data of X-ray images and image data of the DSA images by performing X-ray imaging on the object P is an example of the X-ray imaging unit described in the claims.

[7] While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An image analysis device, comprising:
a processor configured to
acquire image data of a plurality of sequential DSA images of a same object;
calculate a parameter value per pixel, using time variation of pixel values at a same region of the object among the plurality of sequential DSA images;
generate a single parametric image in which a color in accordance with the parameter value is allocated per pixel corresponding to the same region of the object; and
generate a plurality of parametric time phase images from the single parametric image and the calculated parameter value, each pixel of each of the plurality of parametric time phase images having a color converted from the color of a corresponding pixel of the single parametric image, by using the calculated parameter value.

2. The image analysis device according to claim 1, wherein
the processor is further configured to generate the plurality of parametric time phase images in such a manner that at least one of luminosity, chroma, and transmittance of each pixel changes between the plurality of parametric time phase images.

3. The image analysis device according to claim 2, further comprising a display configured to display the plurality of parametric time phase images as a color moving image.

4. The image analysis device according to claim 3, wherein
the processor is further configured to specify a region with a changed bloodstream amount based on a subtraction image between the plurality of parametric time phase images.

5. The image analysis device according to claim 4, wherein
the processor is further configured to
acquire the plurality of sequential DSA images, which are imaged before and after an operation; and
calculate a subtraction map between the single parametric image generated based on the DSA images imaged before the operation and the single parametric image generated based on the DSA images imaged after the operation, and to specify the region with the changed bloodstream amount by performing threshold processing on each pixel of the subtraction map.

6. The image analysis device according to claim 4, wherein
the display is configured to distinguishably display the region with the changed bloodstream amount by surrounding the region with the changed bloodstream amount with a frame, in display of the plurality of parametric time phase images.

7. The image analysis device according to claim 4, wherein
the processor is further configured to generate vessel wall emphasis image data in which a vessel wall in the region with the changed bloodstream amount is emphasized; and
the display is configured to distinguishably display the vessel wall based on the vessel wall emphasis image data, in display of the plurality of parametric time phase images.

8. The image analysis device according to claim 1, wherein
the processor is further configured to generate the plurality of parametric time phase images so as to respectively correspond to the sequential DSA images, by performing color conversion in such a manner that at least one of luminosity, chroma, and transmittance of each pixel changes between the plurality of parametric time phase images.

9. The image analysis device according to claim 1, wherein
the processor is further configured to specify a region with a changed bloodstream amount based on a subtraction image between the plurality of parametric time phase images; and
the image analysis device further includes a display configured to display the plurality of parametric time phase images as a color moving image.

10. The image analysis device according to claim 9, wherein
the display is configured to distinguishably display the region with the changed bloodstream amount by surrounding the region with the changed bloodstream amount with a frame, in display of the plurality of parametric time phase images.

11. The image analysis device according to claim 9, wherein
the display is configured to distinguishably display the region with the changed bloodstream amount by blinking the region with the changed bloodstream amount, in display of the plurality of parametric time phase images.

12. The image analysis device according to claim 9, wherein
the display is configured to distinguishably display the region with the changed bloodstream amount by displaying only the region with the changed bloodstream amount with gray-scale and displaying all other regions in color, in display of the plurality of parametric time phase images.

13. The image analysis device according to claim 9, wherein the processor is further configured to generate vessel wall emphasis image data in which a vessel wall in the region with the changed bloodstream amount is emphasized; and the display is further configured to distinguishably display the vessel wall based on the vessel wall emphasis image data, in display of the plurality of parametric time phase images.

14. An X-ray diagnostic apparatus, comprising:

X-ray imaging circuitry configured to generate projection data of X-ray images by detecting X-rays passing through an object before and after administration of a contrast agent, and to generate image data of a plurality of sequential DSA images of the object based on each subtraction between an X-ray image before administration of the contrast agent and each of sequential X-ray images obtained after administration of the contrast agent; and the image analysis device according to claim 1 configured to calculate the parameter value per pixel, using the time variation of the pixel values of the respective sequential DSA images, to generate the single parametric image in which the color in accordance with the parameter value is allocated per pixel, and to generate the plurality of the parametric time phase images from the single parametric image and the calculated parameter value, each pixel of each of the plurality of the parametric time phase images having a color converted from the color of a corresponding pixel of the single parametric image, by using the calculated parameter value.

* * * * *